US00PP27703P3

(12) United States Plant Patent
Sato

(10) Patent No.: US PP27,703 P3
(45) Date of Patent: Feb. 21, 2017

(54) ***BIDENS* PLANT NAMED 'SUNBIDEVB 2'**

(50) Latin Name: *Bidens ferulifolia*
Varietal Denomination: Sunbidevb 2

(71) Applicant: Kazunori Sato, Tokyo (JP)

(72) Inventor: Kazunori Sato, Tokyo (JP)

(73) Assignee: Suntory Flowers Limited, Tokyo (JP)

( * ) Notice: Subject to any disclaimer, the term of this patent is extended or adjusted under 35 U.S.C. 154(b) by 100 days.

(21) Appl. No.: 14/545,150

(22) Filed: Mar. 31, 2015

(65) Prior Publication Data

US 2016/0295790 P1 Oct. 6, 2016

(51) Int. Cl.
*A01H 5/02* (2006.01)

(52) U.S. Cl.
USPC ..... Plt./410

(58) Field of Classification Search
USPC ..... Plt./263.1, 410
See application file for complete search history.

*Primary Examiner* — Susan McCormick Ewoldt
*Assistant Examiner* — Karen Redden
(74) *Attorney, Agent, or Firm* — C. A. Whealy

(57) ABSTRACT

A new and distinct cultivar of *Bidens* plant named 'Sunbidevb 2', characterized by its upright and mounding plant habit; vigorous growth habit; freely branching habit; freely flowering habit; year-round flowering habit; during the summer, inflorescences have yellow orange and bright orange red-colored ray florets; and good garden performance.

1 Drawing Sheet

Botanical designation: *Bidens ferulifolia.*
Cultivar denomination: 'SUNBIDEVB 2'.

BACKGROUND OF THE INVENTION

The present invention relates to a new and distinct cultivar of *Bidens* plant, botanically known as *Bidens ferulifolia* and hereinafter referred to by the name 'Sunbidevb 2'.

The new *Bidens* plant is a product of a planned breeding program conducted by the Inventor in Fukaya, Saitama, Japan. The objective of the breeding program is to create new *Bidens* plants with year-round flowering habit and numerous attractive inflorescences.

The new *Bidens* plant originated from a cross-pollination made by the Inventor in Fukaya, Saitama, Japan in December, 2008 of two unnamed proprietary selections of *Bidens ferulifolia*, not patented. The new *Bidens* plant was discovered and selected by the Inventor as a single flowering plant from within the progeny of the stated cross-pollination in a controlled greenhouse environment in Fukaya, Saitama, Japan in July, 2011.

Asexual reproduction of the new *Bidens* plant by vegetative cuttings in a controlled environment in Fukaya, Saitama, Japan since July, 2011 has shown that the unique features of this new *Bidens* plant are stable and reproduced true to type in successive generations.

SUMMARY OF THE INVENTION

Plants of the new *Bidens* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Sunbidevb 2'. These characteristics in combination distinguish 'Sunbidevb 2' as a new and distinct *Bidens* plant:

1 Upright and mounding plant habit.
2. Vigorous growth habit.
3. Freely branching habit.
4. Freely flowering habit.
5. Year-round flowering habit.
6. During the summer, inflorescences have yellow orange and bright orange red-colored ray florets; during the spring and autumn, inflorescences have bright orange red-colored ray florets; and during the winter, inflorescences have dark reddish brown-colored ray florets.
7. Good garden performance.

Plants of the new *Bidens* differ primarily from plants of the female parent selection in the following characteristics:

1. Inflorescences of plants of the new *Bidens* have more ray florets than inflorescences of plants of the female parent selection.
2. Plants of the new *Bidens* and the female parent selection differ in ray floret color as plants of the female parent selection have bright yellow-colored ray florets.

Plants of the new *Bidens* differ primarily from plants of the male parent selection in the following characteristics:

1. Plants of the new *Bidens* are broader than plants of the male parent selection.
2. Plants of the new *Bidens* flower freely year-round whereas plants of the male parent selection do not flower freely during the summer.
3. Plants of the new *Bidens* and the male parent selection differ in ray floret color as plants of the male parent selection have yellow-colored ray florets.

Plants of the new *Bidens* can be compared to plants of *Bidens ferulifolia* 'Danyel9', disclosed in U.S. Plant Pat. No. 20,968. In side-by-side comparisons conducted in Higashiomi, Shiga, Japan, plants of the new *Bidens* differed from plants of 'Danyel9' in the following characteristics:

1. Plants of the new *Bidens* were more vigorous than plants of 'Danyel9'.
2. Plants of the new *Bidens* were broader than plants of 'Danyel9'.
3. Plants of the new *Bidens* had larger leaves than plants of 'Danyel9'.
4. Plants of the new *Bidens* flowered freely year-round whereas plants of 'Danyel9' did not flower freely during the summer.
5. Plants of the new *Bidens* and 'Danyel9' differed in ray floret color as plants of 'Danyel9' had yellow-colored ray florets.
6. Plants of the new *Bidens* did not produce seeds whereas plants of 'Danyel9' produced seeds.

BRIEF DESCRIPTION OF THE PHOTOGRAPHS

The accompanying photographs illustrate the overall appearance of the new *Bidens* plant showing the colors as true as it is reasonably possible to obtain in colored reproductions of this type. Colors in the photographs may differ slightly from the color values cited in the detailed botanical description which accurately describe the colors of the new *Bidens* plant.

The photograph at the top of the sheet comprises a side perspective view of a typical flowering plant of 'Sunbidevb 2' grown in a container.

The photograph at the bottom of the sheet is a close-up view of a typical flowering plant of 'Sunbidevb 2'.

DETAILED BOTANICAL DESCRIPTION

The aforementioned photographs and following observations and measurements describe plants grown in 18-cm containers during the summer in an outdoor nursery in Higashiomi, Shiga, Japan and under cultural practices typical of commercial *Bidens* production. During the production of the plants, day temperatures ranged from 20° C. to 30° C. and night temperatures ranged from 10° C. to 20° C. Plants were four and three months old when the photographs and description, respectively, were taken. In the following description, color references are made to The Royal Horticultural Society Colour Chart, 2007 Edition, except where general terms of ordinary dictionary significance are used.

Botanical classification: *Bidens ferulifolia* 'Sunbidevb 2'.

Parentage:

*Female parent.*—Unnamed proprietary selection of *Bidens ferulifolia*, not patented.

*Male parent.*—Unnamed proprietary selection of *Bidens ferulifolia*, not patented.

Propagation:

*Type.*—By vegetative cuttings.

*Time to initiate roots, summer.*—About seven days at temperatures ranging from 20° C. to 25° C.

*Time to initiate roots, winter.*—About ten days at temperatures ranging from 12° C. to 15° C.

*Time to produce a rooted young plant, summer.*—About ten days at temperatures ranging from 20° C. to 25° C.

*Time to produce a rooted young plant, winter.*—About two weeks at temperatures ranging from 12° C. to 15° C.

*Root description.*—Fibrous; white in color.

*Rooting habit.*—Freely branching.

Plant description:

*Plant and growth habit.*—Upright and mounding plant habit; vigorous growth habit.

*Branching habit.*—Freely branching habit with numerous primary and secondary lateral branches potentially forming at every node.

*Plant height.*—About 26 cm.

*Plant diameter or spread.*—About 72 cm.

*Lateral branches.*—Length: About 18.1 cm. Diameter: About 1.3 mm. Internode length: About 3 cm. Strength: Strong. Texture: Smooth, glabrous. Color: Close to 146C strongly tinted with close to 165A.

Leaf description:

*Arrangement.*—Opposite, simple.

*Length.*—About 4.3 cm.

*Width.*—About 2.5 cm.

*Shape.*—Roughly deltoid; pinnatisect.

*Apex.*—Acute.

*Base.*—Truncate.

*Margin.*—Serrate.

*Texture, upper surface.*—Smooth, glabrous.

*Texture, lower surface.*—Sparsely pubescent.

*Venation pattern.*—Pinnate, reticulate.

*Color.*—Developing and fully expanded leaves, upper surface: Close to 137D; venation, close to 137D. Developing and fully expanded leaves, lower surface: Close to 138B; venation, close to 138C.

*Petioles.*—Length: About 1.3 cm. Diameter: About 0.6 mm. Texture, upper and lower surfaces: Sparsely pubescent. Color, upper and lower surfaces: Close to 144B tinted with close to 176B.

Inflorescence description:

*Appearance.*—Single (daisy) inflorescence form with ray and disc florets forming acropetally on a receptacle; inflorescences positioned above and beyond the foliar plane on strong peduncles; inflorescences face mostly upright.

*Flowering habit.*—Freely flowering habit with about 200 inflorescences developing per plant.

*Fragrance.*—Moderately fragrant.

*Natural flowering season.*—Plants flower year-round in Japan; plants begin flowering about eight weeks after planting.

*Inflorescence longevity.*—Individual inflorescences last about seven to ten days on the plant; inflorescences not persistent.

*Inflorescence buds.*—Height: About 8 mm. Diameter: About 5.2 mm. Shape: Globose. Color: Close to 173A; towards the base, close to N144B.

*Inflorescence size.*—Diameter: About 3.2 cm. Depth (height): About 9.4 mm. Disc diameter: About 5.9 mm. Receptacle diameter: About 3.5 mm. Receptacle height: About 0.8 mm. Receptacle color: Close to 145B.

*Ray florets.*—Number of ray florets per inflorescence: About six to eight arranged in a single whorl. Length: About 1.7 cm. Width: About 8.1 mm. Shape: Elliptic. Apex: Rounded and emarginate. Base: Obtuse. Margin: Entire. Texture, upper and lower surfaces: Smooth, glabrous. Color: When opening, upper surface: Towards the base, close to 17A; towards the apex, close to 182A. When opening, lower surface: Close to 13C. Fully opened, upper surface: Towards the base, close to 13A; towards the apex, close to 182A. During the spring and autumn, color is closer to between 169A and 179B, and during the winter, color is closer to 179A. Fully opened, lower surface: Close to 7A.

*Disc florets.*—Number of disc florets per inflorescence: About 70. Shape: Tubular, elongated; apex, five-pointed. Length: About 5.1 mm. Diameter: About 1.4 mm. Color, when opening: Close to 163B. Color, fully opened: Close to 163A.

*Phyllaries.*—Quantity per inflorescence: About eleven in a single whorl. Length: About 3.8 mm. Width: About 1 mm. Shape: Elliptic. Apex: Acute. Base: Truncate. Margin: Entire. Texture, upper and lower surfaces: Smooth, glabrous. Color, upper and lower surfaces: Close to 137B.

*Peduncles.*—Length, terminal peduncle: About 7.2 cm. Diameter: About 1 mm. Strength: Strong; flexible. Aspect: Upright to outwardly, inflorescences held above and beyond the foliar plane. Texture: Smooth, glabrous. Color: Close to 146A tinted with close to 183A.

*Reproductive organs.*—Androecium: Present on disc florets only. Quantity per disc floret: Five. Filament length: About 2.1 mm. Filament color: Close to 1C. Anther shape: Ellipsoidal. Anther length: About 2.1 mm. Anther color: Close to 165A; towards the apex, close to 4C. Pollen amount: Moderate. Pollen color: Close to 14A. Gynoecium: Present on ray and disc florets. Pistil length: About 4 mm. Style length: About 3.2 mm. Style color: Close to 1C. Stigma shape: Bifurcate; apex curled outwardly. Stigma color: Close to 15A. Ovary color: Close to 144D.

*Seeds.*—Seed development has not been observed on plants of the new *Bidens*.

Disease & pest resistance: Plants of the new *Bidens* have not been shown to be resistant to pathogens and pests common to *Bidens* plants.

Garden performance: Plants of the new *Bidens* have exhibited good garden performance and to tolerate rain, wind and temperatures ranging from 5° C. to 35° C.

It is claimed:

1. A new and distinct *Bidens* plant named 'Sunbidevb 2' as illustrated and described.

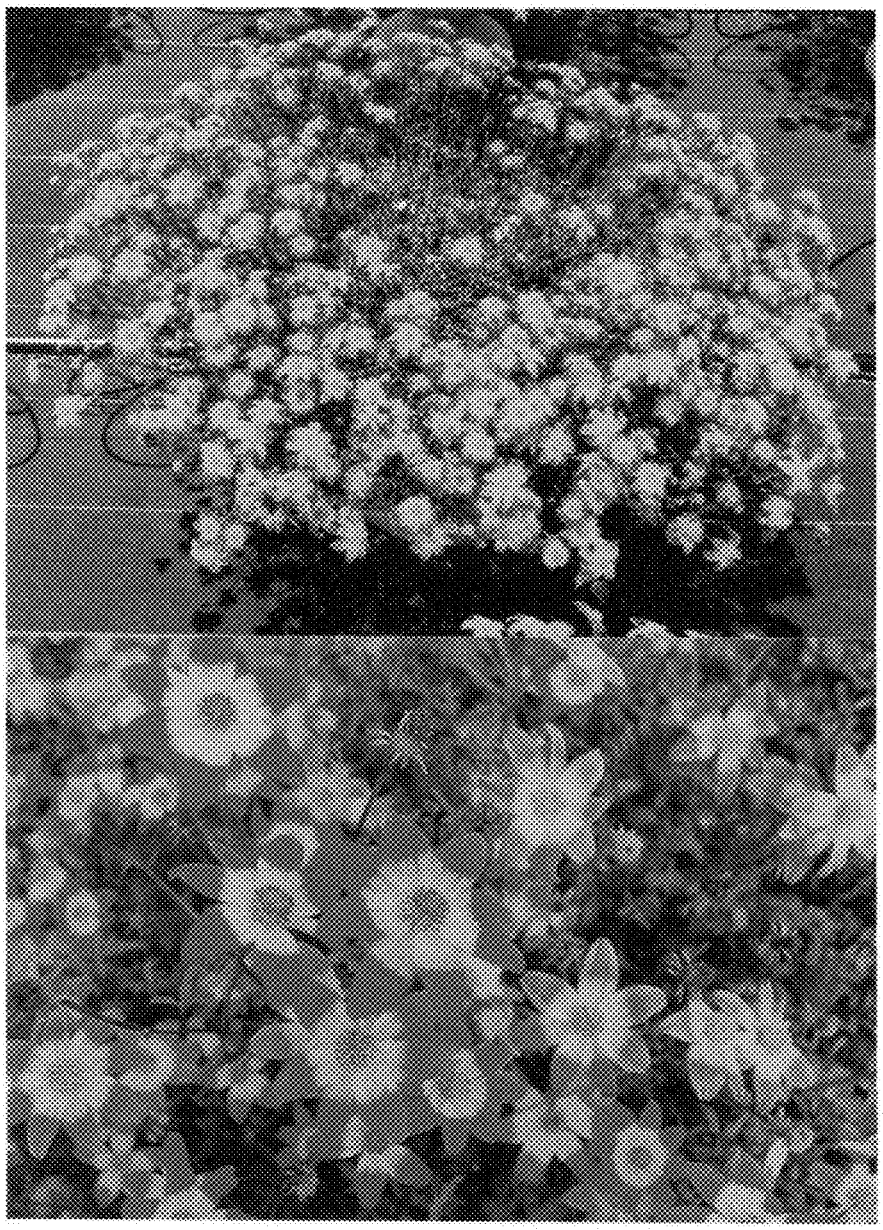

* * * * *